(12) United States Patent
Moshe

(10) Patent No.: US 6,967,721 B2
(45) Date of Patent: Nov. 22, 2005

(54) METHOD AND DEVICE FOR NON-INVASIVELY OPTICALLY DETERMINING BULK DENSITY AND UNIFORMITY OF WEB CONFIGURED MATERIAL DURING IN-LINE PROCESSING

(75) Inventor: Danny S. Moshe, Kiryat Ono (IL)

(73) Assignee: AM-Vision Technologies Ltd., Tel Aviv (IL)

( * ) Notice: Subject to any disclaimer, the term of this patent is extended or adjusted under 35 U.S.C. 154(b) by 363 days.

(21) Appl. No.: 10/399,750

(22) PCT Filed: Oct. 23, 2001

(86) PCT No.: PCT/IL01/00978

§ 371 (c)(1),
(2), (4) Date: Apr. 22, 2003

(87) PCT Pub. No.: WO02/35308

PCT Pub. Date: May 2, 2002

(65) Prior Publication Data

US 2004/0042011 A1    Mar. 4, 2004

Related U.S. Application Data

(60) Provisional application No. 60/242,060, filed on Oct. 23, 2000.

(51) Int. Cl.[7] ............................................. G01N 21/84
(52) U.S. Cl. .................... 356/430; 356/431; 356/237.1; 356/238.1; 356/238.2
(58) Field of Search .................................. 356/429, 430, 356/431, 237.1, 238.1, 238.2, 238.5, 242.1

(56) References Cited

U.S. PATENT DOCUMENTS

| | | | | |
|---|---|---|---|---|
| 3,678,268 A | * | 7/1972 | Reim et al. .................... | 378/54 |
| 3,980,891 A | * | 9/1976 | Slaker ......................... | 356/431 |
| 3,987,660 A | * | 10/1976 | Pelanne ....................... | 356/432 |
| 4,680,205 A | * | 7/1987 | Lerner et al. ................ | 356/429 |
| 5,982,498 A | * | 11/1999 | Byatt et al. .................. | 356/429 |
| 5,991,046 A | * | 11/1999 | Shakespeare et al. ........ | 356/429 |
| 6,137,294 A | * | 10/2000 | Best et al. ................... | 324/640 |

* cited by examiner

Primary Examiner—Layla G. Lauchman
Assistant Examiner—Juan D. Valentin, II

(57) ABSTRACT

Method and device for non-invasively optically determining bulk density and uniformity of web material during in-line processing, by measuring and analyzing light scattered by volume segments of transported web material. Influence of process operating parameters of temperature, volumetric bulk material transport rate, type, and, physicochemical characteristics and properties, of the transported web material, on collecting and detecting the scattered light, are used for process correcting raw measured values of scattered light flux density/energy of scattered light exiting volume segments of the transported web material, for determining bulk density and uniformity. Pattern recognition and classification techniques are performed using the calculated bulk density and uniformity values of the web material. Bulk density is determined in the approximate range of from one to zero kilogram per square meter of web material, with corresponding measuring sensitivity of about one gram per square meter of web material.

49 Claims, 1 Drawing Sheet

METHOD AND DEVICE FOR NON-INVASIVELY OPTICALLY DETERMINING BULK DENSITY AND UNIFORMITY OF WEB CONFIGURED MATERIAL DURING IN-LINE PROCESSING

This application claims the benefit of Provisional Application No. 60/242,060, filed Oct. 23, 2000.

FIELD AND BACKGROUND OF THE INVENTION

The present invention relates to determining density and uniformity of web configured material, and more particularly, to a method and device for non-invasively optically determining bulk density and uniformity of web configured material during in-line processing, based on measuring and analyzing light scattered by entire volume segments of the web configured material.

Manufacturing of a wide variety of consumer products, in a wide variety of industries, involves in-line processing of web configured materials. This includes in-line processing of web configured materials at an early, intermediate, advanced, or final stage in the overall manufacturing sequence leading to a finished product. In particular, raw materials, or, early, intermediate, advance, or final stage materials may be of a web configuration, whereby downstream manufacturing requires in-line processing of such web configured materials, eventually leading to production of the finished product.

Herein, the term 'web configured material', also referred to as 'web material', refers to any material, natural or synthetic, organic and/or inorganic, pure or mixed, whose external macro, bulk, or processing configuration or structure, in contrast to internal micro or local configuration or structure, is at least partly a web or is web-like, featuring or characterized by a uniform or non-uniform latticed, woven, interwoven, or interlaced configuration or structure. Commonly known web configured materials are natural raw materials such as wool, cotton, and flax used for manufacturing a countless number of finished products in a wide variety of industries, and, early, intermediate, advanced, or final stage materials such as natural or synthetic (for example, nylon) yarn used for manufacturing cloth, textile fabrics, feminine hygiene products, medical gauze, paper, plastic, and related products, where any of these products may also be early, intermediate, advance, or final stage materials used in an overall manufacturing sequence.

In such manufacturing sequences, web configured material exiting one process is transported by an in-line conveyor for entering another process. In going from one process to another process in a given manufacturing sequence, bulk density, and consequently, uniformity, throughout the entire volume of the web configured material may change, according to the particular operating or processing parameters of the processes involved. At this stage of the manufacturing sequence, bulk density and uniformity are often important properties of the web configured material which need to be determined, monitored, and controlled prior to the web configured material entering further downstream processes or storage. In particular, if the bulk density and/or uniformity of a given web configured material are outside of established quality control values, use of such web configured material is expected to lead to downstream intermediate, advanced, or final stage materials, or stored web configured material, similarly failing their established quality control values, potentially causing undesirable rejection of material, manufacturing down time and added cost to the finished product.

Microwave techniques, known from the prior art, are available for non-invasively determining bulk density and/or uniformity of web configured materials, such as wool and cotton, during in-line processing. In these teachings, typically, a radiation source beam is transmitted through a portion of material and is received by a receiving antenna, which then produces a signal characteristic of the material. Microwave signal parameters such as attenuation and phase shift are used to determine bulk density and/or uniformity of the material. Such techniques are applicable to relatively high bulk density loose or packaged materials, for example, having bulk densities of on the order of several kilograms per square meter, with corresponding measuring sensitivities significantly less than desirable for many current manufacturing sequences involving in-line processing of web configured materials. In particular, cost and quality of many current manufacturing sequences involving in-line processing of web configured materials could be significantly improved if there was to exist the capability of determining and monitoring bulk density in the range of from about one kilogram to essentially zero kilogram, with corresponding measuring sensitivity of the order of one gram per square meter.

There are also teachings of applying infrared spectroscopy for non-invasively determining bulk density and/or uniformity of web configured materials during in-line processing. Typically, exposed surface area of web configured material passing between manufacturing processes is subjected to an infrared beam, whose output is compared to the output of a reference or calibration beam, for obtaining in-line values of infrared reflections proportional to density and/or uniformity of the material. In practice, these teachings are significantly limited by interference during the infrared measurements, caused by the presence of varying quantities of dirt on the surface of the infrared source and receiver apparatus, and dust in the surrounding air. Moreover, such techniques are additionally limited by the infrared measurements providing information relating only to the exposed surface area of the web configured material during in-line processing, and are not capable of providing bulk density or uniformity information relating to entire volume segments of the moving web configured material. Especially for low bulk density web configured material, results of bulk density and/or uniformity obtained by such prior art techniques are significantly limited.

Aside from radiation based methods and devices, currently available methods and devices for non-invasively determining bulk density, and consequently, uniformity, of web configured material during in-line processing are typically based on measuring operating parameters, such as humidity and temperature in the immediate vicinity of the material, for determining the moisture content of the web configured material. Here, for a given temperature, the moisture content of the web configured material is proportional to bulk density, and consequently, uniformity, of the web configured material during the in-line processing. These techniques are also applicable to relatively high bulk density loose or packaged materials, having bulk densities of on the order of several kilograms per square meter, and feature relatively low measuring sensitivities.

To one of ordinary skill in the art, there is thus a need for, and it would be highly advantageous to have a method and device for non-invasively determining bulk density and uniformity of web configured material during in-line processing, featuring the capability of determining bulk density in the range of from about one kilogram to essentially zero kilogram per square meter of web configured material, with corresponding measuring sensitivity of on the order of one gram per square meter of web configured material.

Accordingly, there is thus a need for, and it would be highly advantageous to have a method and device for non-invasively optically determining bulk density and uniformity of web configured material during in-line processing, based on measuring and analyzing light scattered by entire volume segments of the web configured material during the in-line processing. Such a method and device providing accurate and precise determination of bulk density and uniformity of web configured material during in-line processing would enable achieving significantly higher levels of process optimization and control, quality control and quality assurance, and resource savings, associated with individual manufacturing processes, leading to achieving the same improvements in a large number of overall manufacturing sequences currently used for producing consumer products involving in-line processing of web configured materials.

SUMMARY OF THE INVENTION

The present invention relates to a method and device for non-invasively optically determining bulk density and uniformity of web configured material during in-line processing, based on measuring and analyzing light scattered by entire volume segments of the web configured material during the in-line processing.

It is therefore an object of the present invention to provide a method and device for non-invasively optically determining density and uniformity of web configured material during in-line processing.

It is a further object of the present invention to provide such a method and device which are based on measuring and analyzing light scattered by entire volume segments of the web configured material during the in-line processing, and determining bulk density and uniformity of the web configured material from the measurements of scattered light.

It is another object of the present invention to provide such a method and device which are also based on using empirically determined measurements and data of operating parameters of temperature of the web configured material temperature, volumetric bulk material transport rate of the web configured material, type of the web configured material, and physicochemical characteristics and properties of the web configured material, for process correcting raw measured values of scattered light flux density or energy of the scattered light exiting the volume segments of the web configured material, for calculating highly accurate and precise bulk density values and uniformity values of the web configured material.

It is another object of the present invention to provide such a method and device where the bulk density values and uniformity values of the web configured material are analyzed by pattern recognition and classification techniques, for obtaining information useful to quality control and quality assurance of manufacturing sequences involving in-line processing of web configured material.

It is a further object of the present invention to provide such a method and device capable of determining bulk density in the range of from about one kilogram to essentially zero kilogram per square meter of web configured material, with corresponding measuring sensitivity of on the order of one gram per square meter of web configured material.

Thus, according to the present invention, there is provided a method for non-invasively optically determining bulk density and uniformity of web configured material during in-line processing, comprising the steps of: (a) illuminating a volume segment of the web configured material situated on and transported by a transport mechanism during the in-line processing, by light exiting an illumination mechanism of an optical unit, whereby (i) part of the light interacts with and is scattered by the volume segment of the web configured material, forming web material scattered light, (ii) part of the light passes through the volume segment of the web configured material, forming through web material light, and, (iii) part of the light is reflected by the volume segment of the web configured material and by the material transport mechanism, forming reflected light; (b) collecting and detecting (i) at least part of the web material scattered light, by a primary light collector-detector of the optical unit, forming a plurality of detected web material scattered light, (ii) at least part of the through web material light, by the primary light collector-detector of the optical unit, forming detected through web material light, and, (iii) at least part of the reflected light, by a reflected light collector-detector of the optical unit, forming detected reflected light; (c) converting (i) the plurality of detected web material scattered light into a corresponding plurality of web material scattered light raw electrical signals, raw signal set $(S)^{raw}$, by the primary light collector-detector, (ii) the detected through web material light into a corresponding through web material light raw electrical signal, raw signal set $(TM)^{raw}$, by the primary light collector-detector, and, (iii) the detected reflected light into a corresponding reflected light raw electrical signal, raw signal set $(R)^{raw}$, by the reflected light collector-detector; (d) sending (i) the plurality of web material scattered light raw electrical signals, raw signal set $(S)^{raw}$, (ii) the through web material light raw electrical signal, raw signal set $(TM)^{raw}$, and, (iii) the reflected light raw electrical signal, raw signal set $(R)^{raw}$, to a central programming and data/information processing unit for analysis and processing; (e) process correcting (i) the plurality of web material scattered light raw electrical signals, raw signal set $(S)^{raw}$, (ii) the through web material light raw electrical signal, raw signal set $(TM)^{raw}$, and, (iii) the reflected light raw electrical signal, raw signal set $(R)^{raw}$, by the central programming and data/information processing unit, thereby forming (i) a web material scattered light process corrected signal set, $(S)^{PC}$, (ii) a through web material light process corrected signal set, $(TM)^{PC}$, and, (iii) a reflected light process corrected signal set, $(R)^{PC}$; and (f) calculating a value of the bulk density of the web configured material from (i) the web material scattered light process corrected signal set, $(S)^{PC}$, (ii) the through web material light process corrected signal set, $(TM)^{PC}$, and, (iii) the reflected light process corrected signal set, $(R)^{PC}$, by the central programming and data/information processing unit.

According to another aspect of the present invention, there is provided a device for non-invasively optically determining bulk density and uniformity of web configured material during in-line processing, comprising: (a) an optical unit including an illumination mechanism emitting light illuminating a volume segment of the web configured material situated on and transported by a transport mechanism during the in-line processing, whereby (i) part of the light interacts with and is scattered by the volume segment of the web configured material, forming web material scattered light, (ii) part of the light passes through the volume segment of the web configured material, forming through web material light, and, (iii) part of the light is reflected by the volume segment of the web configured material and by the material transport mechanism, forming reflected light; (b) a primary light collector-detector of the optical unit for collecting and detecting (i) at least part of the web material scattered light, for forming a plurality of detected web material scattered light, and, converting the plurality of detected web material scattered light into a corresponding plurality of web material scattered light raw electrical signals, raw signal set $(S)^{raw}$, and, collecting and detecting (ii) at least part of the through web material light, for forming detected through web material light, and, converting the detected through web material light into a corresponding through web material light raw electrical signal, raw signal set $(TM)^{raw}$; (c) a reflected light collector-detector of the optical unit for collecting and detecting (iii) at least part of the reflected light, for forming detected reflected light, and, converting the detected reflected light into a corresponding reflected light raw electrical signal, raw signal set $(R)^{raw}$; and (d) a central programming and data/information processing unit for analysis and process correcting (i) the plurality of web material scattered light raw electrical signals, raw signal set $(S)^{raw}$, (ii) the through web material light raw electrical signal, raw signal set $(TM)^{raw}$, and, (iii) the reflected light raw electrical signal, raw signal set $(R)^{raw}$, thereby forming (i) a web material scattered light process corrected signal set, $(S)^{PC}$, (ii) a through web material light process corrected signal set, $(TM)^{PC}$, and, (iii) a reflected light process corrected signal set, $(R)^{PC}$, and, for calculating a value of the bulk density of the web configured material from (i) the web material scattered light process corrected signal set, $(S)^{PC}$, (ii) the through web material light process corrected signal set, $(TM)^{PC}$, and, (iii) the reflected light process corrected signal set, $(R)^{PC}$.

According to further features in preferred embodiments of the invention described below, there is (1) the collecting and detecting the at least part of the web material scattered light by the primary light collector-detector featuring a flat mirror reflecting a first fraction of the at least part of the web material scattered light onto a parabolic mirror, whereby a first electro-optical sensor located at focal point of the parabolic mirror detects the first fraction of the at least part of the web material scattered light; (2) the collecting and detecting the at least part of the web material scattered light by the primary light collector-detector featuring at least one additional electro-optical sensor for collecting and detecting a second fraction of the at least part of the web material scattered light; (3) the collecting and detecting the at least part of the through web material light by the primary light collector-detector featuring at least one additional electro-optical sensor; and (4) the collecting and detecting the at least part of the reflected light by the reflected light collector-detector featuring at least one electro-optical sensor.

According to further features in preferred embodiments of the invention described below, the web material scattered light process corrected signal set, $(S)^{PC}$, is a function of terms and parameters of the web material scattered light raw signal set, $(S)^{raw}$, temperature of the web configured material, volumetric bulk material transport rate of the web configured material, type of the web configured material, and, physicochemical characteristics and properties of the web configured material; the through web material light process corrected signal set, $(TM)^{PC}$, is a function of terms and parameters of the web material scattered light raw signal set, $(TM)^{raw}$, temperature of the web configured material, volumetric bulk material transport rate of the web configured material, type of the web configured material, and, physicochemical characteristics and properties of the web configured material; and, the reflected light process corrected signal set, $(R)^{PC}$, is a function of terms and parameters of the reflected light raw signal set, $(R)^{raw}$, temperature of the web configured material, volumetric bulk material transport rate of the web configured material, type of the web configured material, and, physicochemical characteristics and properties of the web configured material.

The method and device of the present invention serve as significant improvements over currently used methods and devices for determining density and uniformity of web configured material during in-line processing, by providing highly accurate and precise values of bulk density and uniformity corresponding to entire volume segments of moving web configured material. This leads to achieving high levels of process optimization and control, quality control and quality assurance, and resource savings, associated with individual manufacturing processes, as well as with a large number of overall manufacturing sequences currently used for producing consumer products involving in-line processing of web configured materials.

BRIEF DESCRIPTION OF THE DRAWING

The invention is herein described, by way of example only, with reference to the accompanying drawing, wherein.

DESCRIPTION OF THE PREFERRED EMBODIMENTS

Figure 1:
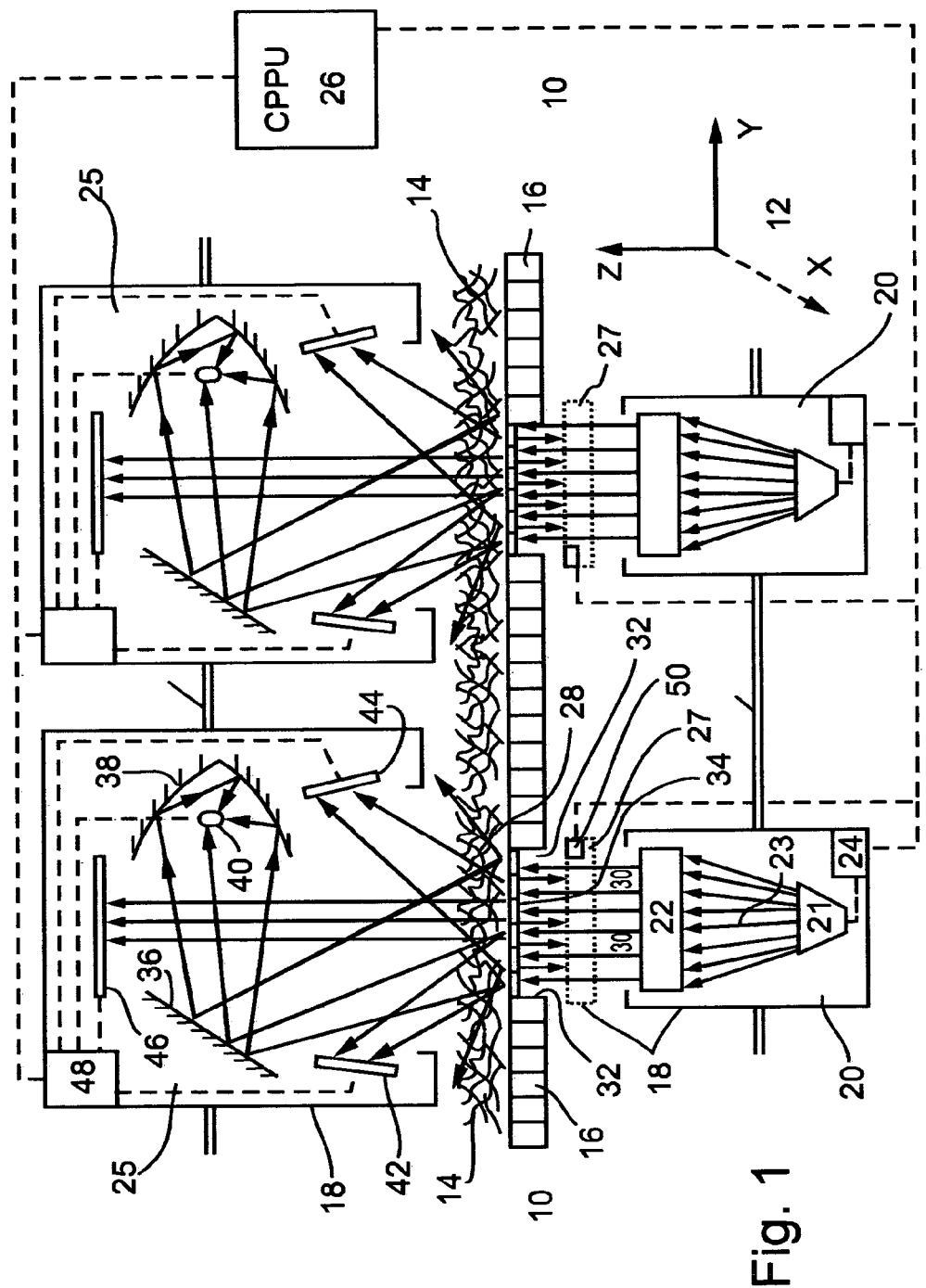
FIG. 1 is a schematic diagram illustrating a cut-away front view of an exemplary preferred embodiment of the device for non-invasively optically determining density and uniformity of web configured material during in-line processing, in accordance with the present invention.

The present invention is of a unique method and device for non-invasively optically determining density and uniformity of web configured material during in-line processing.

As described above, in the present disclosure, the term 'web configured material' refers to any material, natural or synthetic, organic and/or inorganic, pure or mixed, whose external macro, bulk, or processing configuration or structure, in contrast to internal micro or local configuration or structure, is at least partly a web or is web-like, featuring or characterized by a uniform or non-uniform latticed, woven, interwoven, or interlaced configuration or structure. Commonly known web configured materials are natural raw materials such as wool, cotton, and flax used for manufacturing a countless number of finished products in a wide variety of industries, and, early, intermediate, advanced, or final stage materials such as natural or synthetic (for example, nylon) yarn used for manufacturing cloth, textile fabrics, feminine hygiene products, medical gauze, paper, plastic, and related products, where any of these products may also be early, intermediate, advance, or final stage materials used in an overall manufacturing sequence.

The method and device of the present invention are based on detecting and measuring the scattered light flux density, also referred to as the scattered light energy, of scattered light exiting entire volume segments of moving web configured material exposed to a well controlled light source during in-line processing, and using these measurements and empirically determined data of operating parameters for highly accurately and reproducibly calculating bulk density and uniformity of the moving web configured material during the in-line processing.

Empirically determined data relating the influence of operating parameters of temperature of the web configured material, volumetric bulk material transport rate of the web configured material, type of the web configured material, and physicochemical characteristics and properties of the web configured material, on the step of collecting and detecting the scattered light flux density or energy, are used for process correcting raw measured values of scattered light flux density or energy of the scattered light exiting the web configured material, which are subsequently used for determining highly accurate and reproducible values of bulk density and uniformity of the web configured material. Bulk density and uniformity values thus obtained correspond to entire volume segments of the moving web configured material, and are not limited to the exposed surface of the moving web configured material, as taught from the prior art.

It is to be understood that the invention is not limited in its application to the details of the order or sequence of steps of operation or implementation of the method, or, to the details of construction, arrangement, and, composition of the components of the device, set forth in the following description, drawings, or examples. For example, the following description refers to a conveyor as an exemplary material transport mechanism used for transporting web configured material during in-line processing, as part of an overall manufacturing sequence, in order to illustrate implementation of the present invention. The invention is capable of other embodiments or of being practiced or carried out in various ways. Also, it is to be understood that phraseology and terminology employed herein are for the purpose of description and should not be regarded as limiting.

Steps, components, operation, and implementation of a method and device for non-invasively optically determining density and uniformity of web configured material during in-line processing of the web configured material, where the web configured material is situated on, and is transported from process to process by, a material transport mechanism as part of an overall manufacturing sequence, according to the present invention, are better understood with reference to the following description and accompanying drawing. Herein, the term 'web configured material' is also referred to as 'web material'.

Referring now to the drawings, FIG. 1 illustrates a cut-away front view of an exemplary preferred embodiment of the device, generally referred to as device 10, for implementing the method of the present invention. In FIG. 1, reference coordinate system 12 is drawn such that the y-z plane corresponds to the plane of the page and the x-axis (dashed line) extends into and out of the plane of the page. In FIG. 1, web material 14 is situated on a material transport mechanism 16 such as a conveyor, for in-line automatically and controllably, continuously or discontinuously, being transported along the x-axis during in-line processing, as part of an overall manufacturing sequence including multiple processes, where web material 14 is transported from process to process. The volumetric bulk material transport rate of web material 14 transported by material transport mechanism 16 through the manufacturing sequence is set by controlling the configuration or volume of the bulk web material fed onto, and situated on, material transport mechanism 16, and by controlling the linear speed or velocity of material transport mechanism 16, according to the requirements of the manufacturing sequence.

The present invention is implemented by using at least one optical unit 18 featuring main components of (i) an illumination mechanism 20, (ii) a primary light collector-detector 25, and, (iii) a reflected light collector-detector 27 (indicated in FIG. 1 by the dotted line rectangle), where the at least one optical unit 18 is operatively connected to, and in communication with, a central programming and data/information processing unit (CPPU) 26. Illumination mechanism 20 and reflected light collector-detector 27 of optical unit 18 are positioned below material transport mechanism 16, while primary light collector-detector 25 of optical unit 18 is positioned above web material 14, during automatic transport of web material 14.

Preferably, the invention is implemented with a plurality of optical units 18 operatively connected to, and in communication with, CPPU 26. For example, in FIG. 1, two optical units 18 are shown, where each optical unit 18 features illumination mechanism 20, primary light collector-detector 25, and reflected light collector-detector 27, operatively connected to, and in communication with CPPU 26. For clarity of understanding, the following description of the invention is with respect to operation of a single optical unit 18 operatively connected to, and in communication with CPPU 26. It is straightforward for one skilled in the art to extend this description for implementing the method using a plurality of optical units 18.

In FIG. 1, electrical and/or electronic communication between selected components of device 10 and CPPU 26 is indicated by control/data links, shown as dashed lines connecting the selected components with CPPU 26 of device 10.

In Step (a) of the method of the present invention, there is illuminating a volume segment, for example, volume segment 28, of web material 14 situated on transport mechanism 16 with light 30 supplied by illumination mechanism 20 of optical unit 18.

Illumination mechanism 20 includes (i) a light source 21, (ii) a light collimating element 22, such as a collimating lens for collimating light 23 exiting light source 21 in the direction of volume segment 28 of web material 14, (iii) a local illumination mechanism control unit 24 in electronic communication with CPPU 26, and, appropriate control/data links.

Light 30 supplied by illumination mechanism 20, for illuminating web material 14, is selected from the group consisting of polychromatic light, monochromatic light, poly- or multi-monochromatic light, and, combinations thereof. An exemplary polychromatic light is white light. An exemplary inonochromatic light is selected from the group consisting of visible spectrum monochromatic light, such as red light, blue light, or green light, and, invisible spectrum monochromatic light, such as ultra-violet light or infrared light. An exemplary poly- or multi-chromatic light is a combination of a plurality of at least two different previously listed exemplary monochromatic lights. Illumination mechanism 20 is controlled by a local illumination mechanism control unit 24 in electronic communication with CPPU 26.

An opening or gap 32 in material transport mechanism 16, bridged by a supporting element 34 made of sufficiently strong material having appropriate dimensions and configuration for supporting web material 14 during the in-line processing, and substantially transparent to light 30 supplied by illumination mechanism 20, enables light 30 exiting illumination mechanism 20 to illuminate volume segment 28 of web material 14.

During Step (a), the following takes place, (i) part of light 30 exiting illumination mechanism 20 interacts with and is scattered by volume segment 28 of web material 14, forming web material scattered light, (ii) part of light 30 exiting illumination mechanism 20 passes through volume segment 28 of web material 14, forming through web material light, and, (iii) part of light 30 exiting illumination mechanism 20 is reflected by volume segment 28 of web material 14 and by material transport mechanism 16, forming reflected light.

In Step (b) there is collecting and detecting (i) at least part of the web material scattered light, by primary light collector-detector 25 of optical unit 18, forming a plurality of detected web material scattered light, (ii) at least part of the through web material light, by primary light collector-detector 25 of optical unit 18, forming detected through web material light, and, (iii) at least part of the reflected light, by reflected light collector-detector 27 of optical unit 18, forming detected reflected light.

In sub-step (i) of Step (b), the collecting and detecting the at least part of the web material scattered light is performed by primary light collector-detector 25 featuring a flat mirror 36 reflecting a first fraction of the part of the web material scattered light onto a parabolic mirror 38, in order that a first electro-optical sensor 40 located at the focal point of parabolic mirror 38 detects the fraction of the part of the web material scattered light. There is additionally collecting and detecting a second fraction of the at least part of the web material scattered light, by primary light collector-detector 25 featuring at least one additional electro-optical sensor, for example, a second electro-optical sensor 42 and a third electro-optical sensor 44. Sub-step (i) of Step (b) results in forming the plurality of detected web material scattered light, according to synchronized operation of first electro-optical sensor 40, second electro-optical sensor 42, and, third electro-optical sensor 44.

In sub-step (ii) of Step (b), the collecting and detecting the at least part of the through web material light is performed by primary light collector-detector 25 featuring at least one additional electro-optical sensor, for example, a fourth electro-optical sensor 46.

In sub-step (iii) of Step (b), the collecting and detecting the at least part of the reflected light is performed by reflected light collector-detector 27 featuring at least one electro-optical sensor, for example, a fifth electro-optical sensor (not shown in FIG. 1 for the purpose of clarity).

Design and operation of the components of optical unit 18, in general, and, components of primary light collector-detector 25 and reflected light collector-detector 27, in particular, are such that the majority of light 30 exiting illumination mechanism 20 interacts with and is scattered by volume segment 28 of web material 14, forming a relatively high fraction of web material scattered light. Moreover, preferably, the majority of web material scattered light is reflected by flat mirror 36 onto parabolic mirror 38, in order that first electro-optical sensor 40 located at the focal point of parabolic mirror 38 detects the largest fraction of the part of the web material scattered light.

In Step (c) there is converting (i) the plurality of detected web material scattered light into a corresponding plurality of web material scattered light raw electrical or electronic signals, raw signal set $(S)^{raw}$, by primary light collector-detector 25, (ii) the detected through web material light into a corresponding through web material light raw electrical or electronic signal, raw signal set $(TM)^{raw}$, by primary light collector-detector 25, and, (iii) the detected reflected light into a corresponding reflected light raw electrical or electronic signal, raw signal set $(R)^{raw}$, by reflected light collector-detector 27.

Converting detected light into electrical or electronic signals, according to (i) and (ii) of Step (c), is effected by a first signal converter and transfer mechanism 48, operating as part of primary light collector-detector 25. Converting detected light into electrical or electronic signals, according to (iii) of Sep (c), is effected by a second signal converter and transfer mechanism 50, operating as part of reflected light collector-detector 27.

In Step (d) there is sending (i) the plurality of web material scattered light raw electrical signals, raw signal set $(S)^{raw}$, by first signal converter and transfer mechanism 48, (ii) the through web material light raw electrical signal, raw signal set $(TM)^{raw}$, by first signal converter and transfer mechanism 48, and, (iii) the reflected light raw electrical signal, raw signal set $(R)^{raw}$, by second signal converter and transfer mechanism 50, to central programming and data/information processing unit (CPPU) 26 for analysis and processing.

Step (c) and Step (d) are enabled by connecting the various indicated components of device 10 by control/data links (indicated in FIG. 1 by dashed lines drawn between the indicated components of device 10).

In Step (e) there is process correcting (i) the plurality of web material scattered light raw electrical signals, raw signal set $(S)^{raw}$, (ii) the through web material light raw electrical signal, raw signal set $(TM)^{raw}$, and, (iii) the reflected light raw electrical signal, raw signal set $(R)^{raw}$, by central programming and data/information processing unit (CPPU) 26.

During in-line processing of web material 14, measurement of several operating parameters, in the vicinity of volume segment 28 of moving web material 14, is required for accurately and reliably determining bulk density and uniformity of continuously moving web material 14. Operating parameters affecting the determining of bulk density and uniformity of web material 14 include (1) the temperature of web material 14, (2) the volumetric bulk material transport rate of web material 14 transported by material transport mechanism 16 between processes, where this operating parameter is a function of the configuration or volume of bulk web material 14 fed onto, and situated on, material transport mechanism 16, and a function of the linear speed or velocity of material transport mechanism 16, (3) the type of web material 14, for example, natural or synthetic, in general, wool, cotton, flax, or yarn, in particular, as described above, and, (4) physicochemical characteristics and properties, such as the internal micro or local density, and shape, of web material 14 subjected to the in-line processing.

Process correcting of the raw electrical signals obtained from Step (d) is performed in order to account for the affects, typically, non-linear in nature, of in-line processing operating parameters during Step (b) of collecting and detecting (i) the plurality of detected web material scattered light, (ii) the through web material light, and, (iii) the detected reflected light.

Calibration and process related empirical data obtained and stored according to operating device 10 as described above, are used in the step of process correcting the raw electrical signal sets, $(S)^{raw}$, $(TM)^{raw}$, and, $(R)^{raw}$, by CPPU 26. Calibration and process related empirical data features, for example, determinations of bulk density and uniformity made during conditions involving well characterized and controlled in-line processing operating parameters of (1) the temperature, hereinafter referred to as T(web), of web material 14, (2) the volumetric bulk material transport rate, hereinafter referred to as $V_{Bulk}$(web), of web material 14 transported by material transport mechanism 16, during the in-line processing, where $V_{Bulk}$(web) is a function of the configuration or volume of bulk web material 14 fed onto, and situated on, material transport mechanism 16, and a function of the linear speed or velocity of material transport mechanism 16, (3) the type, hereinafter referred to as Y(web), of web material 14, and, (4) physicochemical characteristics and properties, hereinafter referred to as P(web), of web material 14, subjected to the in-line processing. For example, P(web) is a function of the internal micro or local density, and shape, among other physicochemical characteristics and properties, of web material 14.

In particular, according to a functional relationship featuring each raw electrical signal set and the operating parameters of the in-line processing, the raw electrical signal sets are process corrected for forming process corrected electrical signal sets as follows:

$$(S)^{PC} = F_{PC1}[(S)^{raw}, T(web), V_{Bulk}(web), Y(web), P(web)],$$

$$(TM)^{PC} = F_{PC2}[(TM)^{raw}, T(web), V_{Bulk}(web), Y(web), P(web)], \text{ and}$$

$$(R)^{PC} = F_{PC3}[(R)^{raw}, T(web), V_{Bulk}(web), Y(web), P(web)].$$

In these relations, $F_{PC1}$ is a function featuring linear and/or non-linear terms and parameters of the web material scattered light raw signal set $(S)^{raw}$, T(web), $V_{Bulk}$(web), Y(web), and, P(web); $F_{PC2}$ is a function featuring linear and/or non-linear terms and parameters of the through web material light raw signal set $(TM)^{raw}$, T(web), $V_{Bulk}$(web), Y(web), and, P(web); and, $F_{PC3}$ is a function featuring linear and/or non-linear terms and parameters of the reflected light raw signal set $(R)^{raw}$, T(web), $V_{Bulk}$(web), Y(web), and, P(web).

Step (e) results in forming (i) a web material scattered light process corrected signal set, $(S)^{PC}$, (ii) a through web material light process corrected signal set, $(TM)^{PC}$, and, (iii) a reflected light process corrected signal set, $(R)^{PC}$.

In Step (f) there is calculating a bulk density value of web material 14 from (i) the web material scattered light process corrected signal set, $(S)^{PC}$, (ii) the through web material light process corrected signal set, $(TM)^{PC}$, and, (iii) the reflected light process corrected signal set, $(R)^{PC}$, by central programming and data/information processing unit (CPPU) 26.

In sub-step (i) of Step (f) there is calculating a scattered light flux density value, also referred to as a scattered light energy value, $E_S$(web), of web material 14, from a first formula including terms and parameters corresponding to process corrected signal set, $(S)^{PC}$, process corrected signal set, $(TM)^{PC}$, and, process corrected signal set, $(R)_{PC}$. Accordingly, a preferred embodiment of the first formula is:

$$E_S(web) = F_1[(S)^{PC}, (TM)^{PC}, (R)^{PC}],$$

where $F_1$ is a function featuring linear and/or non-linear terms and parameters of the scattered light process corrected signal set, $(S)^{PC}$, the through web material process corrected signal set, $(TM)^{PC}$, and, the reflected light process corrected signal set, $(R)^{PC}$.

In sub-step (ii) of Step (f) there is calculating a reference light flux density value, also referred to as a reference light energy value, $E_0$(ref), proportional to the total amount of light 30 exiting illumination mechanism 20 of optical unit 18, from a second formula including terms and parameters corresponding to a set of operating parameters of illumination mechanism 20, herein, referred to as (IM), process corrected signal set, $(S)^{PC}$, process corrected signal set, $(TM)^{PC}$, and, process corrected signal set, $(R)^{PC}$. Accordingly, a preferred embodiment of the second formula is:

$$E_0(ref) = F_2[(IM), (S)^{PC}, (TM)^{PC}, (R)^{PC}],$$

where $F_2$ is a function featuring linear and/or non-linear terms and parameters of the set (IM) of operating parameters of the illumination mechanism, the scattered light process corrected signal set, $(S)^{PC}$, the through web material process corrected signal set, $(TM)^{PC}$, and, the reflected light process corrected signal set, $(R)^{PC}$.

In sub-step (iii) of Step (f) there is calculating the bulk density value, $D_{bulk}$(web), of web material 14, from a third formula including terms and parameters corresponding to the reference light energy value, $E_0$(ref), of light 30 exiting illumination mechanism 20 of optical unit 18, and, the scattered light energy value, $E_S$(web), of web material 14. Accordingly, a preferred embodiment of the third formula is:

$$D_{bulk}(web) = F_3[E_0(ref), E_S(web)],$$

where $F_3$ is a function featuring linear and/or non-linear terms and parameters of the reference light energy value, $E_0$(ref), and, the scattered light energy value, $E_S$(web). For implementation, an exemplary form of the function $F_3$ is: $F_3 = K [E_0(ref)/E_S(web)]$, where K is an empirically determined constant. Accordingly, the bulk density value, $D_{bulk}$(web), of web material 14, is calculated using $F_3$ as follows:

$$D_{bulk}(web) = K[E_0(ref)/E_S(web)].$$

The method and device of the present invention are capable of determining bulk density in the range of from about one kilogram to essentially zero kilogram per square meter of web material, with corresponding measuring sensitivity of on the order of one gram per square meter of web material.

In Step (g) there is calculating a uniformity value, U(web), of web material 14, from at least two bulk density values, $D_{bulk}$(web), determined from Step (f), by central programming and data/information processing unit (CPPU) 26.

In particular, there is calculating a uniformity value U(web), of web material 14, passing through device 10, from at least two bulk density values, $D_{bulk}$(web, $t_i$), determined from Step (f), as a continuous or discontinuous function of time, t, at corresponding times, $t_i$. Step (g) enables generating a time profile of bulk density values, $D_{bulk}$(web, $t_i$), and, a time profile of uniformity values, $U_t$(web), of web material 14 passing through device 10 during the in-line processing.

In Step (h) there is performing pattern recognition and classification techniques using a plurality of the calculated bulk density values, $D_{bulk}$(web), of web material 14, determined from Step (f), and a plurality of the uniformity values, U(web), of web material 14, determined from Step (g).

Examples of specific pattern recognition and classification techniques and algorithms suitable for application to the method of the present invention are described in U.S. Pat. No. 5,880,830, issued to Schechter, and in U.S. Pat. No. 6,091,843, issued to Horesh et al., and references cited therein, for example, P. Yu. V. Anastassopoulos and A. N. Venetsanopoulos, "Pattern Classification And Recognition Based On Morphology And Neural Networks", *Can. J. Elect. and Comp. Eng.*, Vol. 17 No. 2 (1992), p. 58–59, and the references therein, which are incorporated by reference for all purposes as if fully set forth herein.

Applying pattern recognition and classification techniques enables identifying, classifying, and, analyzing specific characteristics of regions of web material 14 during the in-line processing. Exemplary specific characteristics of regions of web material 14 are high density spots in web material 14, uniformity problems in web material 14, and air holes in web material 14. The information and data obtained are applicable and useful for improving quality control and quality assurance of a manufacturing sequence involving in-line processing of web material 14.

In Step (i), there is repeating Step (a) through Step (h) for each pre-determined time interval, Δt. Accordingly, following each pre-determined time interval, Δt, there is generating a statistical analysis report describing time variation of the density values, $D_{bulk}$(web), of web material 14, determined from Step (f), and of the uniformity values, U(web), of web material 14, determined from Step (g).

While the invention has been described in conjunction with specific embodiments thereof, it is evident that many alternatives, modifications and variations will be apparent to those skilled in the art.

What is claimed is:

1. A method for non-invasively optically determining bulk density and uniformity of web configured material during in-line processing, comprising the steps of:

(a) illuminating a volume segment of the web configured material situated on and transported by a transport mechanism during the in-line processing, by light exiting an illumination mechanism of an optical unit, whereby (i) part of said light interacts with and is scattered by said volume segment of the web configured material, forming web material scattered light, (ii) part of said light passes through said volume segment of the web configured material, forming through web material light, and, (iii) part of said light is reflected by said volume segment of the web configured material and by said material transport mechanism, forming reflected light;

(b) collecting and detecting (i) at least part of said web material scattered light, by a primary light collector-detector of said optical unit, forming a plurality of detected web material scattered light, (ii) at least part of said through web material light, by said primary light collector-detector of said optical unit, forming detected through web material light, and, (iii) at least part of said reflected light, by a reflected light collector-detector of said optical unit, forming detected reflected light;

(c) converting (i) said plurality of detected web material scattered light into a corresponding plurality of web material scattered light raw electrical signals, raw signal set $(S)^{raw}$, by said primary light collector-detector, (ii) said detected through web material light into a corresponding through web material light raw electrical signal, raw signal set $(TM)^{raw}$, by said primary light collector-detector, and, (iii) said detected reflected light into a corresponding reflected light raw electrical signal, raw signal set $(R)^{raw}$, by said reflected light collector-detector;

(d) sending (i) said plurality of web material scattered light raw electrical signals, raw signal set $(S)^{raw}$, (ii) said through web material light raw electrical signal, raw signal set $(TM)^{raw}$, and, (iii) said reflected light raw electrical signal, raw signal set $(R)^{raw}$, to a central programming and data/information processing unit for analysis and processing;

(e) process correcting (i) said plurality of web material scattered light raw electrical signals, raw signal set $(S)^{raw}$, (ii) said through web material light raw electrical signal, raw signal set $(TM)^{raw}$, and, (iii) said reflected light raw electrical signal, raw signal set $(R)^{raw}$, by said central programming and data/information processing unit, thereby forming (i) a web material scattered light process corrected signal set, $(S)^{PC}$, (ii) a through web material light process corrected signal set, $(TM)^{PC}$, and, (iii) a reflected light process corrected signal set, $(R)^{PC}$; and (f) calculating a value of the bulk density of the web configured material from (i) said web material scattered light process corrected signal set, $(S)^{PC}$, (ii) said through web material light process corrected signal set, $(TM)^{PC}$, and, (iii) said reflected light process corrected signal set, $(R)^{PC}$, by said central programming and data/information processing unit.

2. The method of claim 1, whereby said illumination mechanism of said optical unit includes: (i) a light source, (ii) a light collimating element for collimating said light exiting said light source in direction of said volume segment, (iii) a local illumination mechanism control unit in electronic communication with said central programming and data/information processing unit, and, control/data links.

3. The method of claim 1, whereby said light supplied by said illumination mechanism of said optical unit is selected from the group consisting of polychromatic light, monochromatic light, poly- or multi-monochromatic light, and, combinations thereof.

4. The method of claim 1, whereby said light supplied by said illumination mechanism of said optical unit is polychromatic light, said polychromatic light is white light.

5. The method of claim 1, whereby said light supplied by said illumination mechanism of said optical unit is monochromatic light, said monochromatic light is selected from the group consisting of visible spectrum monochromatic light, and, invisible spectrum monochromatic light.

6. The method of claim 1, whereby said light supplied by said illumination mechanism of said optical unit is poly- or multi-monochromatic light, said poly- or multi-monochromatic light is a combination of a plurality of at least two different monochromatic lights selected from the group consisting of visible spectrum monochromatic light, invisible spectrum monochromatic light, and, combinations thereof.

7. The method of claim 1, whereby said material transport mechanism includes an opening bridged by a supporting element supporting the web configured material during the in-line processing, said supporting element is substantially transparent to said light supplied by said illumination mechanism.

8. The method of claim 1, whereby said primary light collector-detector features a plurality of electro-optical sensors for said collecting and detecting said at least part of said web material scattered light.

9. The method of claim 1, whereby said primary light collector-detector features a plurality of electro-optical sensors for said collecting and detecting said at least part of said web material scattered light and for said collecting and detecting said at least part of said through web material light.

10. The method of claim 1, whereby, in step (b), said collecting and detecting said at least part of said web material scattered light is performed by said primary light collector-detector featuring a flat mirror reflecting a fraction of said part of said web material scattered light onto a parabolic mirror, whereby an electro-optical sensor located at focal point of said parabolic mirror detects said fraction of said part of said web material scattered light.

11. The method of claim 1, whereby, in step (b), said collecting and detecting said at least part of said web material scattered light is performed by said primary light collector-detector featuring at least one electro-optical sensor, whereby each said electro-optical sensor detects a fraction of said part of said web material scattered light.

12. The method of claim 1, whereby, in step (b), said collecting and detecting said at least part of said web material scattered light is performed by said primary light collector-detector featuring a flat mirror reflecting a first fraction of said at least part of said web material scattered light onto a parabolic mirror, whereby a first electro-optical sensor located at focal point of said parabolic mirror detects said first fraction of said at least part of said web material scattered light, and, by said primary light collector-detector featuring at least one additional electro-optical sensor, whereby said at least one additional electro-optical sensor collects and detects a second fraction of said at least part of said web material scattered light.

13. The method of claim 1, whereby, step (b) further comprises:
(1) said collecting and detecting said at least part of said web material scattered light by said primary light collector-detector featuring a flat mirror reflecting a first fraction of said at least part of said web material scattered light onto a parabolic mirror, whereby a first electro-optical sensor located at focal point of said parabolic mirror detects said first fraction of said at least part of said web material scattered light;
(2) said collecting and detecting said at least part of said web material scattered light by said primary light collector-detector featuring at least one additional electro-optical sensor for collecting and detecting a second fraction of said at least part of said web material scattered light;
(3) said collecting and detecting said at least part of said through web material light by said primary light collector-detector featuring at least one additional electro-optical sensor;
and
(4) said collecting and detecting said at least part of said reflected light by said reflected light collector-detector featuring at least one electro-optical sensor.

14. The method of claim 13, whereby majority of said web material scattered light is reflected by said flat mirror onto said parabolic mirror, whereby said first fraction is largest fraction of said at least part of said web material scattered light.

15. The method of claim 1, whereby step (c) and step (d) each includes operation of at least one signal converter and transfer mechanism.

16. The method of claim 1, whereby in step (e), said web material scattered light process corrected signal set, $(S)^{PC}$, is a function of terms and parameters of said web material scattered light raw signal set, $(S)^{raw}$, temperature of the web configured material, volumetric bulk material transport rate of the web configured material, type of the web configured material, and, physicochemical characteristics and properties of the web configured material; said through web material light process corrected signal set, $(TM)^{PC}$, is a function of terms and parameters of said web material scattered light raw signal set, $(TM)^{raw}$, temperature of the web configured material, volumetric bulk material transport rate of the web configured material, type of the web configured material, and, physicochemical characteristics and properties of the web configured material; and, said reflected light process corrected signal set, $(R)^{PC}$, is a function of terms and parameters of said reflected light raw signal set, $(R)^{raw}$, temperature of the web configured material, volumetric bulk material transport rate of the web configured material, type of the web configured material, and, physicochemical characteristics and properties of the web configured material.

17. The method of claim 1, whereby step (f) further comprises the steps of:
(1) calculating a scattered light flux density or energy value, $E_S(web)$, of the web configured material, from a first function including terms and parameters corresponding to said process corrected signal set, $(S)^{PC}$, said process corrected signal set, $(TM)^{PC}$, and, said process corrected signal set, $(R)^{PC}$;
(2) calculating a reference light flux density or energy value, $E_0(ref)$, proportional to total amount of said light exiting said illumination mechanism of said optical unit, from a second function including terms and parameters corresponding to a set of operating parameters of said illumination mechanism, (IM), said process corrected signal set, $(S)^{PC}$, said process corrected signal set, $(TM)^{PC}$, and, said process corrected signal set, $(R)^{PC}$;
and
(3) calculating the bulk density value, $D_{bulk}(web)$, of the web configured material, from a third function including terms and parameters corresponding to said reference light energy value, $E_0(ref)$, and said scattered light energy value, $E_S(web)$.

18. The method of claim 17, whereby said first function includes terms and parameters selected from the group consisting of linear terms, non-linear terms, linear parameters, non-linear parameters, and combinations thereof, corresponding to said process corrected signal set, $(S)^{PC}$, said process corrected signal set, $(TM)^{PC}$, and, said process corrected signal set, $(R)^{PC}$.

19. The method of claim 17, whereby said second function includes terms and parameters selected from the group consisting of linear terms, non-linear terms, linear parameters, non-linear parameters, and combinations thereof, corresponding to said set of operating parameters of said illumination mechanism, (IM), said process corrected signal set, $(S)^{PC}$, said process corrected signal set, $(TM)^{PC}$, and, said process corrected signal set, $(R)^{PC}$.

20. The method of claim 17, whereby said third function includes terms and parameters selected from the group consisting of linear terms, non-linear terms, linear parameters, non-linear parameters, and combinations thereof, corresponding to said reference light energy value, $E_0(ref)$, and said scattered light energy value, $E_S(web)$.

21. The method of claim 17, whereby the bulk density value, $D_{bulk}(web)$, is calculated from a said third function equal to K [said $E_0(ref)$/said $E_S(web)$], where said K is an empirically determined constant.

22. The method of claim 1 further comprising step (g), calculating a value of the uniformity of the web configured material from said calculated value of the bulk density of the web configured material as a function of time, by said central programming and data/information processing unit.

23. The method of claim 1 further comprising step (h), performing pattern recognition and classification techniques using a plurality of said calculated bulk density values, $D_{bulk}(Web)$.

24. The method of claim 22 further comprising performing pattern recognition and classification techniques using a plurality of said calculated bulk density values, $D_{bulk}(web)$, and using a plurality of said uniformity values, $U(web)$, of the web configured material.

25. The method of claim 1, whereby the web configured material is a type of material selected from the group consisting of a natural material, a synthetic material, an organic material, an inorganic material, a pure material, a mixed material, and combinations thereof, whose external structure is characterized as at least partly a web or web-like.

26. A device for non-invasively optically determining bulk density and uniformity of web configured material during in-line processing, comprising:

(a) an optical unit including an illumination mechanism emitting light illuminating a volume segment of the web configured material situated on and transported by a transport mechanism during the in-line processing, whereby (i) part of said light interacts with and is scattered by said volume segment of the web configured material, forming web material scattered light, (ii) part of said light passes through said volume segment of the web configured material, forming through web material light, and, (iii) part of said light is reflected by said volume segment of the web configured material and by said material transport mechanism, forming reflected light;

(b) a primary light collector-detector of said optical unit for collecting and detecting (i) at least part of said web material scattered light, for forming a plurality of detected web material scattered light, and, converting said plurality of detected web material scattered light into a corresponding plurality of web material scattered light raw electrical signals, raw signal set $(S)^{raw}$, and, collecting and detecting (ii) at least part of said through web material light, for forming detected through web material light, and, converting said detected through web material light into a corresponding through web material light raw electrical signal, raw signal set $(TM)^{raw}$;

(c) a reflected light collector-detector of said optical unit for collecting and detecting (iii) at least part of said reflected light, for forming detected reflected light, and, converting said detected reflected light into a corresponding reflected light raw electrical signal, raw signal set $(R)^{raw}$; and (d) a central programming and data/information processing unit for analysis and process correcting (i) said plurality of web material scattered light raw electrical signals, raw signal set $(S)^{raw}$, (ii) said through web material light raw electrical signal, raw signal set $(TM)^{raw}$, and, (iii) said reflected light raw electrical signal, raw signal set $(R)^{raw}$, thereby forming (i) a web material scattered light process corrected signal set, $(S)^{PC}$, (ii) a through web material light process corrected signal set, $(TM)^{PC}$, and, (iii) a reflected light process corrected signal set, $(R)^{PC}$, and, for calculating a value of the bulk density of the web configured material from (i) said web material scattered light process corrected signal set, $(S)^{PC}$, (ii) said through web material light process corrected signal set, $(TM)^{PC}$, and, (iii) said reflected light process corrected signal set, $(R)^{PC}$.

27. The device of claim 26, whereby said illumination mechanism of said optical unit includes: (i) a light source, (ii) a light collimating element for collimating said light exiting said light source in direction of said volume segment, (iii) a local illumination mechanism control unit in electronic communication with said central programming and data/information processing unit, and, control/data links.

28. The device of claim 26, whereby said light supplied by said illumination mechanism of said optical unit is selected from the group consisting of polychromatic light, monochromatic light, poly- or multi-monochromatic light, and combinations thereof.

29. The device of claim 26, whereby said light supplied by said illumination mechanism of said optical unit is polychromatic light, said polychromatic light is white light.

30. The device of claim 26, whereby said light supplied by said illumination mechanism of said optical unit is monochromatic light, said monochromatic light is selected from the group consisting of visible spectrum monochromatic light, and, invisible spectrum monochromatic light.

31. The device of claim 26, whereby said light supplied by said illumination mechanism of said optical unit is poly- or multi-monochromatic light, said poly- or multi-monochromatic light is a combination of a plurality of at least two different monochromatic lights selected from the group consisting of visible spectrum monochromatic light, invisible spectrum monochromatic light, and, combinations thereof.

32. The device of claim 26, whereby said material transport mechanism includes an opening bridged by a supporting element supporting the web configured material during the in-line processing, said supporting element is substantially transparent to said light supplied by said illumination mechanism.

33. The device of claim 26, whereby said primary light collector-detector includes a plurality of electro-optical sensors for said collecting and detecting said at least part of said web material scattered light.

34. The device of claim 26, whereby said primary light collector-detector includes a plurality of electro-optical sensors for said collecting and detecting said at least part of said web material scattered light and for said collecting and detecting said through web material light.

35. The device of claim 26, whereby said primary light collector-detector includes a flat mirror for reflecting a fraction of said at least part of said web material scattered light onto a parabolic mirror, and includes an electro-optical sensor located at focal point of said parabolic mirror for detecting said fraction of said at least part of said web material scattered light.

36. The device of claim 26, whereby said primary light collector-detector includes at least one electro-optical sensor for collecting and detecting a fraction of said at least part of said web material scattered light.

37. The device of claim 26, whereby said primary light collector-detector includes a flat mirror for reflecting a first fraction of said at least part of said web material scattered light onto a parabolic mirror, and includes a first electro-optical sensor located at focal point of said parabolic mirror for detecting said first fraction of said at least part of said web material scattered light, and, whereby said primary light collector-detector includes at least one additional electro-optical sensor for collecting and detecting a second fraction of said at least part of said web material scattered light.

38. The device of claim 26, whereby said optical unit further comprises:

(1) said primary light collector-detector featuring a flat mirror for reflecting a first fraction of said at least part of said web material scattered light onto a parabolic mirror, and a first electro-optical sensor located at focal point of said parabolic mirror for detecting said first fraction of said at least part of said web material scattered light;

(2) said primary light collector-detector featuring at least one additional electro-optical sensor for collecting and detecting a second fraction of said at least part of said web material scattered light;

(3) said primary light collector-detector featuring at least one additional electro-optical sensor for said collecting and detecting said at least part of said through web material light;
and
(4) said reflected light collector-detector featuring at least one electro-optical sensor for said collecting and detecting said at least part of said reflected light.

39. The device of claim 38, whereby majority of said web material scattered light is reflected by said flat mirror onto said parabolic mirror, whereby said first fraction is largest fraction of said at least part of said web material scattered light.

40. The device of claim 26, whereby said web material scattered light process corrected signal set, $(S)^{PC}$, is a function of terms and parameters of said web material scattered light raw signal set, $(S)^{raw}$, temperature of the web configured material, volumetric bulk material transport rate of the web configured material, type of the web configured material, and, physicochemical characteristics and properties of the web configured material; said through web material light process corrected signal set, $(TM)^{PC}$, is a function of terms and parameters of said web material scattered light raw signal set, $(TM)^{raw}$, temperature of the web configured material, volumetric bulk material transport rate of the web configured material, type of the web configured material, and, physicochemical characteristics and properties of the web configured material; and, said reflected light process corrected signal set, $(R)^{PC}$, is a function of terms and parameters of said reflected light raw signal set, $(R)^{raw}$, temperature of the web configured material, volumetric bulk material transport rate of the web configured material, type of the web configured material, and, physicochemical characteristics and properties of the web configured material.

41. The device of claim 26, whereby said central programming and data/information processing unit:
(1) calculates a scattered light flux density or energy value, $E_S(web)$, of the web configured material, from a first function including terms and parameters corresponding to said process corrected signal set, $(S)^{PC}$, said process corrected signal set, $(TM)^{PC}$, and, said process corrected signal set, $(R)^{PC}$;
(2) calculates a reference light flux density or energy value, $E_0(ref)$, proportional to total amount of said light exiting said illumination mechanism of said optical unit, from a second function including terms and parameters corresponding to a set of operating parameters of said illumination mechanism, (IM), said process corrected signal set, $(S)^{PC}$, said process corrected signal set, $(TM)^{PC}$, and, said process corrected signal set, $(R)^{PC}$;
and
(3) calculates the bulk density value, $D_{bulk}(web)$, of the web configured material, from a third function including terms and parameters corresponding to said reference light energy value, $E_0(ref)$, and said scattered light energy value, $E_S(web)$.

42. The device of claim 41, whereby said first function includes terms and parameters selected from the group consisting of linear terms, non-linear terms, linear parameters, non-linear parameters, and combinations thereof, corresponding to said process corrected signal set, $(S)^{PC}$, said process corrected signal set, $(TM)^{PC}$, and, said process corrected signal set, $(R)^{PC}$.

43. The device of claim 41, whereby said second function includes terms and parameters selected from the group consisting of linear terms, non-linear terms, linear parameters, non-linear parameters, and combinations thereof, corresponding to said set of operating parameters of said illumination mechanism, (IM), said process corrected signal set, $(S)^{PC}$, said process corrected signal set, $(TM)^{PC}$, and, said process corrected signal set, $(R)^{PC}$.

44. The device of claim 41, whereby said third function includes terms and parameters selected from the group consisting of linear terms, non-linear terms, linear parameters, non-linear parameters, and combinations thereof, corresponding to said reference light energy value, $E_0(ref)$, and said scattered light energy value, $E_S(web)$.

45. The device of claim 41, whereby the bulk density value, $D_{bulk}(web)$, is calculated from a said third function equal to K [said $E_0(ref)$/said $E_S(web)$], where said K is an empirically determined constant.

46. The device of claim 26, whereby said central programming and data/information processing unit further calculates a value of the uniformity of the web configured material from said calculated value of the bulk density of the web configured material as a function of time.

47. The device of claim 26, whereby said central programming and data/information processing unit further performs pattern recognition and classification techniques using a plurality of said calculated bulk density values, $D_{bulk}(web)$.

48. The device of claim 46 whereby said central programming and data/information processing unit further performs pattern recognition and classification techniques using a plurality of said calculated bulk density values, $D_{bulk}(web)$, and using a plurality of said uniformity values, U(web), of the web configured material.

49. The device of claim 26, whereby the web configured material is a type of material selected from the group consisting of a natural material, a synthetic material, an organic material, an inorganic material, a pure material, a mixed material, and combinations thereof, whose external structure is characterized as at least partly a web or web-like.

* * * * *